United States Patent
Shibasaki et al.

(10) Patent No.: US 7,563,916 B2
(45) Date of Patent: Jul. 21, 2009

(54) PROCESS FOR PRODUCING AN ALCOHOL OR A SILYL ETHER THEREOF

(75) Inventors: Masakatsu Shibasaki, Mitaka (JP); Motomu Kanai, Tokyo (JP); Daisuke Tomita, Tokyo (JP); Reiko Wada, Tokyo (JP)

(73) Assignee: Takasago International Corporation, Tokyo (JP)

( * ) Notice: Subject to any disclaimer, the term of this patent is extended or adjusted under 35 U.S.C. 154(b) by 508 days.

(21) Appl. No.: 11/363,522

(22) Filed: Feb. 28, 2006

(65) Prior Publication Data

US 2006/0199973 A1 Sep. 7, 2006

(30) Foreign Application Priority Data

Mar. 2, 2005 (JP) ............... 2005-057618

(51) Int. Cl.
C07F 7/04 (2006.01)
C07C 29/38 (2006.01)
(52) U.S. Cl. ...................... 556/438; 562/567
(58) Field of Classification Search ............ None
See application file for complete search history.

(56) References Cited

FOREIGN PATENT DOCUMENTS

JP 2003-311156 11/2003

OTHER PUBLICATIONS

Yamasaki et al., A General Catalytic Allylation Using Allyltrimethoxysilane, J. Amer. Chem. Soc., vol. 124, No. 23, Jun. 2002, pp. 6536-6537.*

Wada, Reiko et al., "Catalytic Enatioselective Allylboration of Ketones", *J. Am. Chem. Soc.*, 2004, vol. 126, pp. 8910-8911.
Yoshida, Jun-ichi et al., "Solid State Reactions of Organopentafluorosilicates with Copper (I) and Copper (II) Salts", *Tetrahedron LEtters*, No. 13, pp. 1141-1144, 1979.

* cited by examiner

*Primary Examiner*—Rosalynd Keys
(74) *Attorney, Agent, or Firm*—Kubovcik & Kubovcik

(57) ABSTRACT

A process for producing an alcohol or a silyl ether thereof of formula (4):

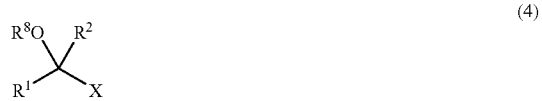

(4)

wherein $R^1$ represents a hydrocarbon, a heterocyclic, or an alkoxycarbonyl group; $R^2$ represents hydrogen or $CO_2R$; X represents an aryl or an alkenyl group of formula (3):

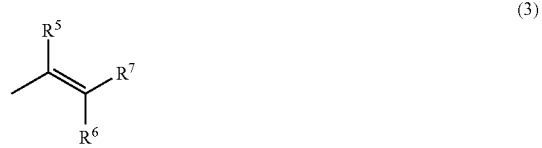

(3)

and $R^8$ represents hydrogen or a silyl residue, by reacting a compound $R^1(C{=}O)R^2$ with a silane $(R^3)_2R^4Si{-}X$, wherein $R^3$ and $R^4$ each represents an alkyl, an alkoxy, or an aryl group; in the presence of (i) a catalyst component containing copper fluoride or a catalyst component containing a copper compound and a fluoride and (ii) a bidentate phosphine compound or in the presence of a complex obtained from the foregoing components.

2 Claims, No Drawings

PROCESS FOR PRODUCING AN ALCOHOL OR A SILYL ETHER THEREOF

TECHNICAL FIELD

The present invention relates to a process for producing an alcohol or a silyl ether thereof from an aldehyde or a 2-oxocarboxylic acid ester and a silicon compound using, as catalyst components, copper and a bidentate phosphine compound. Also, the invention relates to a process for producing an optically active alcohol or a silyl ether thereof by using an optically active substance as the bidentate phosphine compound.

BACKGROUND ART

Alcohols such as allyl alcohols and styrallyl alcohols are useful as intermediates of drugs, agricultural chemicals, and the like. With respect to allyl alcohols, they can be converted into various compounds upon chemical conversion at a double bond site. Furthermore, it is thought that utilities are further widened by converting an alcohol into an optically active substance.

As a method for synthesizing such an optically active alcohol, there are chiefly reported two synthetic methods. One of them is a kinetic resolution method using Sharpless epoxidation, and the other is an asymmetric addition reaction of an alkenylzinc to a carbonyl compound. However, although these two methods are excellent, in the kinetic resolution method, the formation of by-products of a compound of an undesired stereospecific configuration is unavoidable; and in the asymmetric addition reaction of an alkenylzinc, there are encountered problems in application to mass synthesis and safety because this reagent itself is unstable in the presence of air or water. Thus, development of new synthetic methods has been demanded.

In recent years, a reaction using copper as a metal element for catalysts has been keenly studied. For example, there is reported an asymmetric addition reaction of an allyl group to a carbonyl group using a copper catalyst. *J. Am. Chem. Soc.*, 2004, 126, 8910 describes allyboration of a ketone by using copper (II) fluoride/i-Pr-DuPHOS as a catalyst and adding a lanthanoid compound as an additive. Furthermore, JP-A-2003-311156 describes allylation of acetophenone with allyltrimethoxysilane by using copper (I) chloride/tol-BINAP/TBAT as a catalyst.

Furthermore, *Tetrahedron Lett.*, 1979, 13, 1141 describes an addition reaction of an alkenyl group to a carbonyl compound with an alkenylfluorosilane by using a stoichiometric amount of a copper(I) salt, which is, however, not a catalytic reaction.

DISCLOSURE OF THE INVENTION

[Problems that the Invention is to Solve]

However, it cannot be said that the method using a stoichiometric amount of a copper salt is an advantageous method for the reason that a considerable amount of a copper waste is generated or for other reasons. Furthermore, with respect to the reaction using a catalytic amount of copper, although allylation is known, there has not been reported any synthesis method of an alcohol by alkenylation or arylation. Therefore, an object of the invention is to provide an industrially advantageous process for producing an alcohol. In particular, an object of the invention is to provide a process for producing an optically active alcohol which is excellent in optical purity and yield.

[Means for Solving the Problems]

In order to solve the foregoing problems, the present inventors made extensive and intensive investigations. As a result, it has been found that a secondary or tertiary alcohol is obtained industrially advantageously by reacting an aldehyde or a 2-oxocarboxylic acid ester with an alkenylsilane or an arylsilane under a condition where copper is present as a metal element for catalyst and a bidentate phosphine compound is present as a ligand. In addition, it has been found that an optically active alcohol is obtained with high optical purity and good yield by using an optically active substance as a ligand. The invention has thus been completed.

Specifically, the invention is concerned with the following [1] and [2].

[1] A process for producing an alcohol or a silyl ether thereof represented by the following general formula (4):

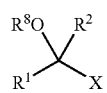

(4)

wherein $R^1$ represents an optionally substituted hydrocarbon group, an optionally substituted heterocyclic group, or an alkoxycarbonyl group; $R^2$ represents a hydrogen atom or $CO_2R$, wherein R represents an alkyl group, an aralkyl group, or an aryl group; X represents an aryl group or an alkenyl group represented by the following general formula (3):

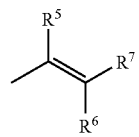

(3)

wherein $R^5$, $R^6$ and $R^7$ each independently represents a hydrogen atom or an alkyl group; and $R^5$ and $R^6$ may be taken together to form a methylene chain; and $R^8$ represents a hydrogen atom or a silyl residue of a silane represented by the following general formula (2):

$$(R^3)_2R^4Si-X \qquad (2)$$

wherein $R^3$ represents an alkyl group or an alkoxy group; $R^4$ represents an alkyl group, an alkoxy group, or an aryl group; and X is the same as defined above, which comprises reacting a compound represented by the following general formula (1):

$$R^1(C=O)R^2 \qquad (1)$$

wherein $R^1$ and $R^2$ are the same as defined above, with the silane represented by the foregoing general formula (2) in the presence of (1) a catalyst component containing copper fluoride or a catalyst component containing a copper compound and a fluoride and (ii) a bidentate phosphine compound, or in the presence of a complex obtained from (i) and (ii).

[2] The process as set forth above in [1], wherein the bidentate phosphine compound is optically active, and the compound of the general formula (4) is an optically active substance.

[Advantage of the Invention]

According to the invention, a secondary or tertiary alcohol can be produced industrially advantageously, and more particularly, with high optical purity and high yield.

[Best Modes for Carrying Out the Invention]

The invention will be hereunder described in detail.

In the production process of the invention, in the compound represented by the general formula (1), as one example of the hydrocarbon group represented by $R^1$, an alkyl group is enumerated. This alkyl group may be linear, branched or cyclic. Examples of the alkyl group include an alkyl group having from 1 to 15 carbon atoms, preferably from 1 to 10 carbon atoms, and more preferably from 1 to 6 carbon atoms. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, and a cyclohexyl group.

Furthermore, these alkyl groups may have a substituent. Examples of the substituent include a hydrocarbon group, an aliphatic heterocyclic group, an aromatic heterocyclic group, an alkoxy group, an alkylenedioxy group, an aryloxy group, an aralkyloxy group, a heteroaryloxy group, a substituted amino group, and a halogen atom.

Examples of the hydrocarbon group which is substituted on the alkyl group include an alkyl group, an alkenyl group, an alkynyl group, an aryl group, and an aralkyl group.

The alkyl group as a substituent of the alkyl group $R^1$ may be linear, branched or cyclic. Examples of the alkyl group include an alkyl group having from 1 to 15 carbon atoms, preferably from 1 to 10 carbon atoms, and more preferably from 1 to 6 carbon atoms. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, and a cyclohexyl group.

The alkenyl group as a substituent of the alkyl group $R^1$ may be linear or branched. Examples of the alkenyl group include an alkenyl group having from 2 to 15 carbon atoms, preferably from 2 to 10 carbon atoms, and more preferably from 2 to 6 carbon atoms. Specific examples thereof include a vinyl group, a propenyl group, a 1-butenyl group, a pentenyl group, and a hexenyl group.

The alkynyl group as a substituent of the alkyl group $R^1$ may be linear or branched. Examples of the alkynyl group include an alkynyl group having from 2 to 15 carbon atoms, preferably from 2 to 10 carbon atoms, and more preferably from 2 to 6 carbon atoms. Specific examples thereof include an ethynyl group, a 1-propynyl group, a 2-propynyl group, a 1-butynyl group, a 3-butynyl group, a pentynyl group, and a hexynyl group.

Examples of the aryl group as a substituent of the alkyl group $R^1$ include an aryl group having from 6 to 14 carbon atoms. Specific examples thereof include a phenyl group, a naphthyl group, an anthryl group, a phenanthryl group, and a biphenyl group.

The aralkyl group as a substituent of the alkyl group $R^1$ is a group in which at least one hydrogen atom of the foregoing alkyl group is substituted with the foregoing aryl group. Examples of the aralkyl group include an aralkyl group having from 7 to 12 carbon atoms. Specific examples thereof include a benzyl group, a 2-phenylethyl group, a 1-phenylpropyl group, and a 3-naphthylpropyl group.

Examples of the aliphatic heterocyclic group as a substituent of the alkyl group $R^1$ include a 5-membered to 8-membered (preferably 5-membered or 6-membered) monocyclic aliphatic heterocyclic group and a polycyclic or fused aliphatic heterocyclic group each having from 2 to 14 carbon atoms and containing, as a heterocyclic atom, at least one (preferably from 1 to 3) hetero atom such as a nitrogen atom, an oxygen atom, and a sulfur atom. Specific examples of the aliphatic heterocyclic group include a pyrrolidinyl-2-one group, a piperidino group, piperazinyl group, a morpholino group, a tetrahydrofuryl group, a tetrahydropyranyl group, and a tetrahydrothienyl group.

Examples of the aromatic heterocyclic group as a substituent of the alkyl group $R^1$ include a 5-membered to 8-membered (preferably 5-membered or 6-membered) monocyclic heteroaryl group and a polycyclic or fused heteroaryl group each having from 2 to 15 carbon atoms and containing, as a heterocyclic atom, at least one (preferably from 1 to 3) hetero atom such as a nitrogen atom, an oxygen atom, and a sulfur atom. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzoimidazolyl group, a benzoxazolyl group, and a benzothiazolyl group.

The alkoxy group as a substituent of the alkyl group $R^1$ may be linear, branched or cyclic. Examples of the alkoxy group include an alkoxy group having from 1 to 6 carbon atoms. Specific examples thereof include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, and a cyclohexyloxy group.

Examples of the alkylenedioxy group as a substituent of the alkyl group $R^1$ include an alkylenedioxy group having from 1 to 3 carbon atoms. Specific examples thereof include a methylenedioxy group, an ethylenedioxy group, a propylenedioxy group, and an isopropylidenedioxy group.

Examples of the aryloxy group as a substituent of the alkyl group $R^1$ include an aryloxy group having from 6 to 14 carbon atoms. Specific examples thereof include a phenyloxy group, a naphthyloxy group, and an anthryloxy group.

Examples of the aralkyloxy group as a substituent of the alkyl group $R^1$ include an aralkyloxy group having from 7 to 12 carbon atoms. Specific examples thereof include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, and a 6-phenylhexyloxy group.

Examples of the heteroaryloxy group as a substituent of the alkyl group $R^1$ include an heteroaryloxy group having from 2 to 14 carbon atoms and containing, as a heterocyclic atom, at least one (preferably from 1 to 3) hetero atom such as a nitrogen atom, an oxygen atom, and a sulfur atom. Specific examples thereof include a 2-pyridyloxy group, a 2-piperazyloxy group, a 2-pyrimidinyloxy group, and a 2-quinolyloxy group.

Examples of the substituted amino group as a substituent of the alkyl group $R^1$ include an amino group in which one or two hydrogen atoms of an amino group are substituted with a substituent such as an alkyl group or an aryl group.

Specific examples of an amino group substituted with an alkyl group, namely an alkyl group-substituted amino group, include a mono- or dialkylamino group such as an N-methylamino group, an N,N-dimethylamino group, an N,N-diethylamino group, an N,N-diisopropylamino group, and an N-cyclohexylamino group.

Specific examples of an amino group substituted with an aryl group, namely an aryl group-substituted amino group, include a mono- or diarylamino group such as an N-phenylamino group, an N,N-diphenylamino group, an N-naphthylamino group, and an N-naphthyl-N-phenylamino group.

Specific examples of an amino group substituted with an aralkyl group, namely an aralkyl group-substituted amino group, include a mono- or diaralkylamino group such as an N-benzylamino group and an N,N-dibenzylamino group.

Examples of the halogen atom as a substituent of the alkyl group $R^1$ include a fluorine atom, a chlorine atom, a bromine atom, and an iodine atom.

Of these substituents, the hydrocarbon group, the aliphatic heterocyclic group, the aromatic heterocyclic group, the alkoxy group, the alkylenedioxy group, the aryloxy group, the aralkyloxy group, the heteroaryloxy group, or the substituted amino group may further be substituted with a group selected from the foregoing group of substituents.

Furthermore, in the compound represented by the general formula (1), as another example of the hydrocarbon group represented by. $R^1$, an alkenyl group having from 2 to 20 carbon atoms, and preferably from 2 to 10 carbon atoms, which may be linear, cyclic or branched, is enumerated. Specific examples of the alkenyl group include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 1-cyclohexenyl group, and a 3-cyclohexenyl group.

Furthermore, these alkenyl groups may have a substituent. Examples of the substituent include an alkyl group, a halogen atom, an aryl group, and a heterocyclic group. Specific examples thereof include those as described previously.

Furthermore, in the compound represented by the general formula (1), as another example of the hydrocarbon group represented by $R^1$, an alkynyl group which may be linear or branched is enumerated. Specific examples thereof include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, and a 5-hexynyl group.

Furthermore, these alkynyl groups may have a substituent. Examples of the substituent include an alkyl group, an aryl group, a heterocyclic group, and a trialkylsilyl group. Specific examples of the alkyl group, the aryl group and the heterocyclic group include those as described previously. Examples of the trialkylsilyl group include trimethylsilyl, triethylsilyl, triisopropylsilyl, tert-butyldimethylsilyl and the like.

Furthermore, in the compound represented by the general formula (1), as another example of the hydrocarbon group represented by $R^1$, an aryl group is enumerated. Specific examples of the aryl group include those as described previously. Furthermore, these aryl group s may have a substituent. Examples of the substituent include an alkyl group, an aryl group, and a heterocyclic group; and specific examples thereof include those described previously.

In the compound represented by the general formula (1), examples of the heterocyclic group represented by $R^1$ include an aliphatic or aromatic heterocyclic group. Specific examples of the heterocyclic group include those as described previously. Furthermore, these heterocyclic groups may have a substituent. Examples of the substituent include an alkyl group, an aryl group, and a heterocyclic group. Specific examples thereof include those as described previously.

In the compound represented by the general formula (1), examples of the alkoxycarbonyl group represented by $R^1$ include an alkoxycarbonyl group having from 2 to 19 carbon atoms. Specific examples thereof include a methoxycarbonyl group, an ethoxycarbonyl group, an n-propoxycarbonyl group, an isopropoxycarbonyl group, an n-butoxycarbonyl group, a tert-butoxycarbonyl group, a pentyloxycarbonyl group, a hexyloxycarbonyl group, a 2-ethylhexyloxycarbonyl group, a lauryloxycarbonyl group, a stearyloxycarbonyl group, a cyclohexyloxycarbonyl group, and a benzyloxycarbonyl group.

In the compound represented by the general formula (1), examples of the alkyl group represented by R of $CO_2R$ include an alkyl group having from 1 to 10 carbon atoms, and preferably from 1 to 6 carbon atoms. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopentyl group, and a cyclohexyl group.

In the compound represented by the general formula (1), examples of the aralkyl group represented by R of $CO_2R$ include a benzyl group, a 4-methoxyphenylmethyl group, and a 1-phenylethyl group.

In the compound represented by the general formula (1), examples of the aryl group represented by R of $CO_2R$ include, a phenyl group, an o-, m- or p-tolyl group and a naphthyl group.

In the invention, in the silane represented by the general formula (2), examples of the alkyl group represented by $R^3$ and $R^4$ include an alkyl group preferably having from 1 to 4 carbon atoms. Specific examples thereof include a methyl group, an ethyl group, an n-propyl group, an isopropyl group, an n-butyl group, a 2-butyl group, an isobutyl group, and a tert-butyl group.

In the invention, in the silane represented by the general formula (2), examples of the alkoxy group represented by $R^3$ and $R^4$ include an alkoxy group preferably having from 1 to 4 carbon atoms. Specific examples thereof include a methoxy group, an ethoxy group, an n-propoxy group, an isopropoxy group, an n-butoxy group, a 2-butoxy group, an isobutoxy group, and a tert-butoxy group.

In the invention, in the silane represented by the general formula (2), examples of the aryl group represented by $R^4$ include an aryl group having from 6 to 14 carbon atoms. Specific examples thereof include a phenyl group, a naphthyl group, an anthryl group, a phenanthryl group, and a biphenyl group. This aryl group may have a substituent. Examples of the substituent which is substituted on the aryl group include an alkyl group, an alkoxy group, a halogen atom, a halogenated alkyl group, a (substituted) amino group, a nitro group, and a cyano group. Specific examples of the substituent include the groups as described previously.

Furthermore, in the silane represented by the general formula (2), examples of the aryl group represented by X include an aryl group having from 6 to 14 carbon atoms. Specific examples thereof include a phenyl group, a naphthyl group, an anthryl group, a phenanthryl group, and a biphenyl group. This aryl group may have a substituent. Examples of the substituent which is substituted on the aryl group include an alkyl group, an alkoxy group, a halogen atom, a halogenated alkyl group, a (substituted) amino group, a nitro group, and a cyano group. Specific examples of the substituent include the groups as described previously.

Furthermore, in the silane represented by the general formula (2), the alkyl group represented by $R^5$, $R^6$ and $R^7$ in the alkenyl group represented by X may be linear, branched or cyclic. Examples of the alkyl group include an alkyl group having from 1 to 15 carbon atoms, preferably from 1 to 10 carbon atoms, and more preferably from 1 to 6 carbon atoms. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, and a cyclohexyl group.

Furthermore, these alkyl groups may have a substituent. Examples of the substituent include an aryl group, an aliphatic heterocyclic group, an aromatic heterocyclic group, an alkoxy group, an alkylenedioxy group, an aryloxy group, an aralkyloxy group, a substituted amino group, and a halogen atom. Specific examples of these groups include the groups as described previously.

Furthermore, in the silane represented by the general formula (2), when $R^5$ and $R^6$ in the alkenyl group represented by X are taken together to form a methylene chain, examples of the methylene chain include a methylene chain such as a methylene group, an ethylene group, a trimethylene group, a tetramethylene group, a pentamethylene group, a propylene group, and an isopropylidene group.

In the production process of the invention, with respect to the compound represented by the general formula (1) and the silane represented by the general formula (2) both of which are used as raw materials, commercially available products may be used as they are. If desired, materials as prepared by properly purifying commercially available products or homemade materials as prepared according to a general process which is known per se may be used.

Next, the catalyst components (i) and (ii) which are used in the invention will be described.

The component (i) is a catalyst component containing copper fluoride or a catalyst component containing a copper compound and a fluoride.

As the catalyst component containing copper fluoride, any material is employable so far as it is a material containing a compound having a bond between a copper atom and a fluorine atom. Above all, a complex between copper fluoride and a phosphine compound, or copper fluoride and a hydrate thereof are preferable. Specific examples thereof include $CuF_nPR_3$ (wherein n represents an integer of from 1 to 3, and R represents an aryl group or an alkyl group) and $CuF_2 \cdot xH_2O$ (wherein x represents an integer)

Furthermore, in the catalyst component containing a copper compound and a fluoride, the copper compound is preferably a monovalent copper compound. Specific examples thereof include CuCl, CuBr, CuI, CuCN, and CuOBu-t.

Examples of the fluoride include $Bu_4NPh_3Si_2F_2$, $Bu_4NF$, $(Me_2N)_3SMe_3SiF_2$, and $(EtO)_3SiF$.

Next, the bidentate phosphine compound which is used in the invention will be described.

Examples of the bidentate phosphine compound which is used in the invention include a phosphine compound represented by the following general formula (5).

$$R^9R^{10}P\text{-}Q\text{-}PR^{11}R^{12} \qquad (5)$$

In the general formula (5), $R^9$, $R^{10}$, $R^{11}$ and $R^{12}$ each independently represents an alkyl group, an aryl group, or a heterocyclic group; and Q represents a spacer.

In the bidentate phosphine compound represented by the general formula (5), the alkyl group may be linear, branched or cyclic. Examples of the alkyl group include an alkyl group having from 1 to 15 carbon atoms, preferably from 1 to 10 carbon atoms, and more preferably from 1 to 6 carbon atoms. Specific examples thereof include a methyl group, an ethyl group, an n-propyl group, an isopropyl group, an n-butyl group, a 2-butyl group, an isobutyl groups a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group, a methylcyclopentyl group, and a methylcyclohexyl group.

Furthermore, in the bidentate phosphine compound represented by the general formula (5), examples of the aryl group include an aryl group having from 6 to 14 carbon atoms. Specific examples thereof include a phenyl group, a naphthyl group, an anthryl group, a phenanthryl group, and a biphenyl group. These aryl groups may have a substituent. Examples of the substituent include an alkyl group, an aryl group, and a heterocyclic group. Specific examples of the substituent include those as described previously.

Furthermore, in the bidentate phosphine compound represented by the general formula (5), examples of the heterocyclic group include an aliphatic or aromatic heterocyclic group. Examples of the aliphatic heterocyclic group include a 5-membered to 8-membered (preferably 5-membered or 6-membered) monocyclic aliphatic heterocyclic group and a polycyclic or fused aliphatic heterocyclic group each having from 2 to 14 carbon atoms and containing, as a heterocyclic atom, at least one hetero atom such as a nitrogen atom, an oxygen atom, and a sulfur atom. Specific examples of the aliphatic heterocyclic group include a pyrrolidyl-2-one group, a piperidino group, piperazinyl group, a morpholino group, a tetrahydrofuryl group, a tetrahydropyranyl group, and a tetrahydrothienyl group.

Examples of the aromatic heterocyclic group include a 5-membered to 8-membered (preferably 5-membered or 6-membered) monocyclic heteroaryl group and a polycyclic or fused heteroaryl group each having from 2 to 15 carbon atoms and containing, as a heterocyclic atom, at least one hetero atom such as a nitrogen atom, an oxygen atom, and a sulfur atom. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzoimidazolyl group, a benzoxazolyl group, and a benzothiazolyl group.

In the bidentate phosphine compound represented by the general formula (5), examples of the spacer represented by Q include an alkylene group and a ferrocenyl group. Examples of the alkylene group include an alkylene group having from 1 to 6 carbon atoms; and specific examples thereof include a methylene group, an ethylene group, a trimethylene group, a tetramethylene group, a pentamethylene group, and a hexamethylene group. As the ferrocenyl group, a ferrocenyl group having a structure of a 1,1'-bisferrocene type is preferable.

Next, the optically active bidentate phosphine compound which is used in the invention will be described.

Examples of the optically active bidentate phosphine compound include optically active bidentate phosphines which were known prior to this application. As one example thereof, a compound having an axially asymmetric structure, which is represented by the following general formula (6), is enumerated.

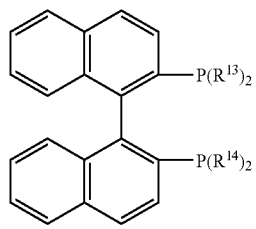

(6)

In the general formula (6), $R^{13}$ and $R^{14}$ may be the same or different and each represents a cyclopentyl group, a cyclohexyl group, or a phenyl group which may be substituted with an alkyl group, an alkoxy group or a halogen atom.

Examples of the alkyl group which is the substituent on the phenyl group include an alkyl group having from 1 to 6 carbon atoms, which may be linear or branched, such as a methyl group, an ethyl group, an n-propyl group, an isopropyl group, an n-butyl group, an isobutyl group, a sec-butyl group, and a tert-butyl group. Examples of the alkoxy group which is the substituent on the phenyl group include an alkoxy group having from 1 to 6 carbon atoms, which may be linear or branched, such as a methoxy group, an ethoxy group, an n-propoxy group, an isopropoxy group, an n-butoxy group, an isobutoxy group, a sec-butoxy group, and a tert-butoxy group. Examples of the halogen atom which is the substituent on the phenyl group include a chlorine atom, a bromine atom, and a fluorine atom. Specific examples of $R^{13}$ and $R^{14}$ include a phenyl group, a p-tolyl group, an m-tolyl group, a 3,5-xylyl group, a p-tert-butylphenyl group, a p-methoxyphenyl group, a 4-methoxy-3,5-di(tert-butyl)phenyl group, a 4-methoxy-3,5-dimethylphenyl group, a p-chlorophenyl group, a cyclopentyl group, and a cyclohexyl group. Furthermore, the binaphthyl ring of the compound represented by the general formula (6) may be substituted with an alkyl group (for example, a methyl group and a tert-butyl group), an alkoxy group (for example, a methoxy group and a tert-butoxy group), a trialkylsilyl group (for example, a trimethylsilyl group, a triisopropylsilyl group, and a tert-butyldimethylsilyl group), or a triarylsilyl group (for example, a triphenylsilyl group).

Specific examples of the optically active bisphosphine represented by the foregoing general formula (6) will be given below, but it should not be construed that the invention is limited thereto. That is, there are enumerated 2,2'-bis(diphenylphosphino)-1,1'-binaphthyl, 2,2'-bis[di(p-tolyl)phosphino]-1,1'-binaphthyl, 2,2'-bis[di(3,5-xylyl)phosphino]-1,1'-binaphthyl, 2,2'-bis[di(3,5-di(tert-butyl)phenyl)phosphino]-1,1'-binaphthyl, 2,2'-bis[di(4-methoxy-3,5-dimethylphenyl)phosphino]-1,1'-binaphthyl, 2,2'-bis[di(4-methoxy-3,5-di(tert-butyl)phenyl)phosphino]-1,1'-binaphthyl, 2,2'-bis(dicyclopentylphosphino)-1,1'-binaphthyl, and 2,2'-bis(dicyclohexylphosphino)-1,1'-binaphthyl.

In addition, as one example of the optically active phosphine having an axially asymmetric structure, a phosphine compound represented by the following general formula (7) is enumerated.

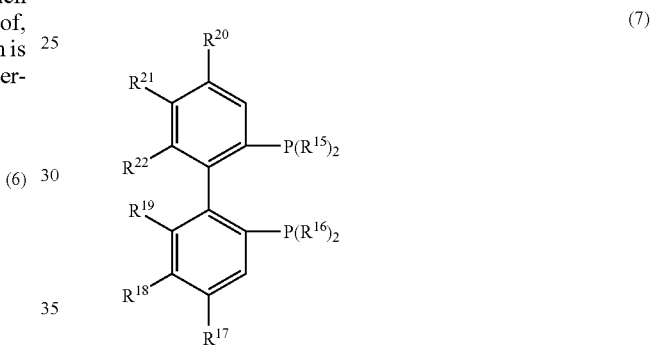

(7)

In the general formula (7), $R^{15}$ and $R^{16}$ may be the same or different and each represents a phenyl group which may be substituted with an alkyl group, an alkoxy group or a halogen atom, a cyclopentyl group, or a cyclohexyl group. $R^{17}$, $R^{18}$, $R^{19}$, $R^{20}$, $R^{21}$ and $R^{22}$ may be the same or different and each represents a hydrogen atom, an alkyl group, an alkoxy group, an acyloxy group, a halogen atom, a haloalkyl group, or a dialkylamino group; two of $R^{17}$, $R^{18}$ and $R^{19}$ may be taken together to form an optionally substituted methylene chain or an optionally substituted polymethylenedioxy group; and two of $R^{20}$, $R^{21}$ and $R^{22}$ may be taken together to form an optionally substituted methylene chain or an optionally substituted polymethylenedioxy group, provided that $R^{19}$ and $R^{22}$ do not represent a hydrogen atom at the same time.

Examples of the alkyl group which is the substituent on the phenyl group include an alkyl group having from 1 to 6 carbon atoms, which may be linear or branched, such as a methyl group and a tert-butyl group; examples of the alkoxy group which is the substituent on the phenyl group include an alkoxy group having from 1 to 6 carbon atoms, which may be linear or branched, such as a methoxy group and a tert-butoxy group; and examples of the halogen atom which is the substituent on the phenyl group include a chlorine atom, a bromine atom, and a fluorine atom. A plural number of these substituents may be substituted on the phenyl group.

Specific examples of $R^{15}$ and $R^{16}$ include a phenyl group, a p-tolyl group, an m-tolyl group, an o-tolyl group, a 3,5-xylyl group, 3,5-di-tert-butylphenyl group, a p-tert-butylphenyl group, a p-methoxyphenyl group, a 3,5-di-tert-butyl-4-methoxyphenyl group, a p-chlorophenyl group, an m-fluorophenyl group, a cyclopentyl group, and a cyclohexyl group.

Furthermore, in $R^{17}$ to $R^{22}$, examples of the alkyl group include an alkyl group having from 1 to 6 carbon atoms, which may be linear or branched, such as a methyl group and a tert-butyl group; examples of the alkoxy group include an alkoxy group having from 1 to 6 carbon atoms, which may be linear or branched, such as a methoxy group and a tert-butoxy group; examples of the acyloxy group include an acetoxy group, a propanoyloxy group, a trifluoroacetoxy group, and a benzoyloxy group; examples of the halogen atom include a chlorine atom, a bromine atom, and a fluorine atom; examples of the haloalkyl group include a haloalkyl group having from 1 to 4 carbon atoms such as a trifluoromethyl group; and examples of the dialkylamino group include a dimethylamino group and a diethylamino group.

When two of $R^{17}$, $R^{18}$ and $R^{19}$ are taken together to form a methylene chain or two of $R^{20}$, $R^{21}$ and $R^{22}$ are taken together to form a methylene chain, the methylene chain is preferably a methylene chain having from 3 to 5 carbon atoms. Specific examples thereof include a trimethylene group, a tetramethylene group, and a pentamethylene group. Furthermore, examples of the substituent of the optionally substituted methylene chain include an alkyl group and a halogen atom. Specific examples thereof include the alkyl group having from 1 to 6 carbon atoms as described previously and a fluorine atom.

When two of $R^{17}$, $R^{18}$ and $R^{19}$ are taken together to form an optionally substituted polymethylenedioxy group or two of $R^{20}$, $R^{21}$ and $R^{22}$ are taken together to form an optionally substituted polymethylenedioxy group, the methylene chain is preferably a methylene chain having from 1 to 3 carbon atoms. Specific examples thereof include a methylene group, an ethylene group, a trimethylene group. Furthermore, examples of the substituent which is substituted on the polymethylenedioxy group include an alkyl group and a halogen atom. Specific examples thereof include the alkyl group having from 1 to 6 carbon atoms as described previously and a fluorine atom.

Specific examples of the optically active phosphine represented by the foregoing general formula (7) will be given below, but it should not be construed that the invention is limited thereto. That is, there are enumerated 2,2'-bis(diphenylphosphino)-5,5', 6,6', 7,7', 8,8'-octahydro-1,1'-binaphthyl (hereinafter referred to as "H8-BINAP"), 2,2'-bis(di-p-tolylphosphino)-5,5', 6,6', 7,7', 8,8'-octahydro-1,1'-binaphthyl, 2,2'-bis(di-m-tolylphosphino)-5,5', 6,6', 7,7', 8,8'-octahydro-1,1'-binaphthyl, 2,2'-bis(di-3,5-xylylphosphino)-5,5', 6,6', 7,7', 8,8'-octahydro-1,1'-binaphthyl, 2,2'-bis(di-p-tert-butylphenylphosphino)-5,5', 6,6', 7,7', 8,8'-octahydro-1,1'-binaphthyl, 2,2'-bis(di-p-methoxyphenylphosphino)-5,5', 6,6', 7,7', 8,8'-octahydro-1,1'- binaphthyl, 2,2'-bis(di-p-chlorophenylphosphino)-5,5', 6,6', 7,7', 8,8'-octahydro-1,1'-binaphthyl, 2,2'-bis(dicyclopentylphosphino)-5,5', 6,6', 7,7', 8,8'-octahydro-1,1'-binaphthyl, 2,2'-bis(dicyclohexylphosphino)-5,5', 6,6', 7,7', 8,8'-octahydro-1,1'-binaphthyl, ((4,4'-bi-1,3-benzodioxole)-5,5'-diyl)bis(diphenylphosphine) (hereinafter referred to as "SEGPHOS"), (4,4'-bi-1,3-benzodioxole)-5,5'-diyl)bis(bis (3,5-dimethylphenyl)phosphine (hereinafter referred to as "DM-SEGPHOS"), ((4,4'-bi-1,3-benzodioxole)-5,5'-diyl)bis(bis(3,5-di-t-butyl-4-methoxyphenyl)phosphine) (hereinafter referred to as "DTBM-SEGPHOS"), ((4,4'-bi-1,3-benzodioxole)-5,5'-diyl)bis(bis (4-methoxyphenyl)phosphine), ((4,4'-bi-1,3-benzodioxole)-5,5'-diyl)bis(dicyclohexylphosphine) (hereinafter referred to as "Cy-SEGPHOS"), ((4,4'-bi-1,3-benzodioxole)-5,5'-diyl)bis(bis(3,5-di-t-butylphenyl)phosphine), 2,2'-bis(diphenylphosphino)-4,4', 6,6'-tetramethyl-5,5'-dimethoxy-1,1'-biphenyl, 2,2'-bis(di-p-methoxyphenylphosphino)-4,4', 6,6'-tetramethyl-5,5'-dimethoxy-1,1'-biphenyl, 2,2'-bis (diphenylphosphino)-4,4', 6,6'-tetra(trifluoromethyl)-5,5'-dimethyl-1,1'-biphenyl, 2,2'-bis(diphenylphosphino)-4,6-di (trifluoromethyl)-4', 6'-dimethyl-5'-methoxy-1,1'-biphenyl, 2-dicyclohexylphosphino-2'-diphenylphosphino-4,4', 6,6'-tetramethyl-5,5'-dimethoxy-1,1'-biphenyl, 2,2'-bis(diphenylphosphino)-6,6'-dimethyl-1,1-biphenyl, 2,2'-bis(diphenylphosphino)-4,4', 6,6'-tetramethyl-1,1'-biphenyl, 2,2'-bis (diphenylphosphino)-3,3', 6,6'-tetramethyl-1,1'-biphenyl), 2,2'-bis(diphenylphosphino)-4,4'-difluoro-6,6'-dimethyl-1, 1'-biphenyl, 2,2'-bis(diphenylphosphino)-4,4'-bis(dimethylamino)-6,6'-dimethyl-1,1'-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 1,11-bis(diphenylphosphino)-5,7-dihydrobenzo[c,e]oxepine, 2,2'-bis(diphenylphosphino)-6,6'-dimethoxy-1,1'-biphenyl, 2,2'-bis (diphenylphosphino)-5,5', 6,6'-tetramethoxy-1,1'-biphenyl, 2,2'-bis(di-p-tolylphosphino)-6,6'-dimethoxy-1,1'-biphenyl, and 2,2'-bis(diphenylphosphino)-4,4', 5,5', 6,6'-hexamethoxy-1,1'-biphenyl.

In addition, examples of other optically active phosphine compounds which can be used include N,N-dimethyl-1-[1', 2-bis(diphenylphosphino)ferrocenyl]ethylamine, 2,3-bis (diphenylphosphino)butane, 1-cyclohexyl-1,2-bis (diphenylphosphino)ethane, 2,3-O-isopropyilidene-2,3-dihydroxy-1,4-bis(diphenylphosphino)butane, 1,2-bis[(o-methoxyphenyl)phenylphosphino]ethane, 1,2-bis(2,5-dimethylphosphorano)benzene, 1,2-bis(2,5-diisopropylphosphorano)benzene, 1,2-bis(2,5-dimethylphosphorano)ethane, 1-(2,5-dimethylphosphorano)-2-(diphenylphosphino)benzene, 5,6-bis(diphenylphosphino)-2-norbornene, N,N'-bis (diphenylphosphino)-N,N'-bis(1-phenylethyl) ethylenediamine, 1,2-bis (diphenylphosphino)propane, and 2,4-bis(diphenylphosphino)pentane. As a matter of course, it should not be construed that the optically active bidentate phosphine compound which can be used in the invention is limited to these examples.

In the production process of the invention, the alcohol represented by the general formula (4) which is the desired substance can be preferably produced by successively adding the compound represented by the general formula (1) and the silane represented by the general formula (2) to a solution containing the catalyst components (i) and (ii) or a solution containing a complex obtained from the catalyst components (i) and (ii) and stirring the mixture at an appropriate reaction temperature for an appropriate reaction time. Alternatively, the catalyst components may be added to the reaction substrate.

The alcohol or a silyl ether thereof which is produced in the invention may be optically active. More specifically, the alcohol or a silyl ether thereof may be an optically active compound represented by the following general formula (4').

(4')

In the general formula (4'), $R^1$, $R^2$, $R^8$ and X are synonymous with those as described previously; and * represents asymmetric carbon.

It is sufficient that the amount of the silane represented by the general formula (2) which is used is from 1 molar time to 10 molar times, and preferably from 1.1 molar times to 5 molar times the amount of the compound represented by the general formula (1).

It is sufficient that the amount of the catalyst component (i) which is used is from 0.01% by mole to 50% by mole, preferably from 1% by mole to 30% by mole, and more preferably from 3% by mole to 20% by mole per mole of copper which is contained in the component (i).

Furthermore, the amount of the fluoride which is used in the component (i) is preferably equal to the mole(s) of copper compound to be used.

It is sufficient to use the bidentate phosphine compound of the component (ii) which is used in an amount of from 1 molar time to 3 molar times, and preferably from 1.5 molar times to 2.5 molar times based on the mole(s) of copper fluoride or copper compound to be used as the component (i).

A reaction solvent is not particularly limited so far as it does not participate in the reaction. Examples thereof include amides such as N,N-dimethylformamide, formamide, and N,N-dimethylacetamide; halogenated hydrocarbons such as dichloromethane, 1,2-dichloroethane, chloroform, carbon tetrachloride, and o-dichlorobenzene; aliphatic hydrocarbons such as pentane, hexane, heptane, octane, decane, and cyclohexane; aromatic hydrocarbons such as benzene toluene and xylene; non-nucleic alcohols such as tert-butanol; ethers such as diethyl ether, diisopropyl ether, tert-butyl methyl ether, dimethoxyethane, ethylene glycol diethyl ether, tetrahydrofuran, 1,4-dioxane, 1,3-dioxolan; and sulfoxides such as dimethyl sulfoxide. Of these solvents, amides such as N,N-dimethylformamide and N,N-dimethylacetamide and dimethylsulfoxide are more preferable. These solvents may be used singly or in an appropriate combination of two or more kinds thereof.

Though the reaction temperature naturally varies depending upon the substrate to be used, it is usually in the range of from −30° C. to 100° C., and preferably from −20° C. to 80° C.

Though the reaction time also naturally varies depending upon the substrate to be used, it is usually from 10 minutes to 100 hours, and preferably from 0.5 hours to 80 hours.

After completion of the reaction, by treating with a desilylating agent which is usually used, such as tetrabutylammonium fluoride (TBAF), it is possible to obtain the alcohol by eliminating the silyl group from the hydroxyl group. Furthermore, it is possible to obtain a desired alcohol by extracting the reaction mixture with a suitable solvent such as ethyl acetate, removing the solvent from the extract, and then performing an operation such as crystallization, distillation and chromatography of every kind singly or in combination.

EXAMPLES

The invention will be hereinunder described in more detail with reference to the following Examples, but it should not be construed that the invention is limited thereto.

Incidentally, an optical purity (ee %) was determined by HPLC (column: CHIRALCEL OJ-H, CHIRALCEL OD-H or CHIRALPAK AD-H (all of which are manufactured by Daicel Chemical Industries, Ltd.), mobile phase: isopropanol/hexane).

Example 1

Synthesis of an Allylic Alcohol:

To a THF (0.3 mL) solution of $CuF.3PPh_3.2EtOH$ (20 mg, 0.02 mmol) as synthesized according to the method described in the publication *Inorg. Chim. Acta*, 1981, 52, 153, and 1,2-bis(diphenylphosphino)ethane (hereinafter abbreviated as "dppe") (12 mg, 0.03 mmol), benzaldehyde (0.020 mL., 0.20 mmol) and vinyltrimethoxysilane (62 μL, 0.40 mmol) were added at room temperature under an argon atmosphere, the temperature was then raised to 60° C., and the mixture was stirred for 3 hours. Thereafter, the reaction mixture was allowed to stand for cooling to room temperature, to which was then added tetrabutylammonium fluoride (TBAF) (1M/THF, 0.5 mL), and the mixture was stirred for 10 minutes. After adding water, the mixture was extracted with ethyl acetate, and the resulting organic layer was washed with saturated brine and then dried over anhydrous sodium sulfate. After drying, the solvent was distilled off, and the residue was subjected to silica gel column chromatography (ethyl acetate/hexane: 1/9 to 1/4), thereby obtaining desired 1-phenyl-2-propen-1-ol in a yield of 61%.

Examples 2 to 5

The results obtained by carrying out the same operations as in Example 1, except for changing the ligand, are shown in Table 1. The abbreviations have the following meanings.

d(p-Cl)ppe:
  1,2-Bis(di-p-chlorophenylphosphino)ethane d(p-MeO)ppe:
  1,2-Bis(di-p-methoxyphenylphosphino)ethane dppp:
  1,3-Bis(diphenylphosphino)propane dppf:
  1,1'-Bis(diphenylphosphino)ferrocene

TABLE 1

| Example | Ligand | Time (h) | Yield (%) |
|---|---|---|---|
| 2 | d(p-Cl)ppe | 24 | 47 |
| 3 | d(p-MeO)ppe | 24 | 57 |
| 4 | dppp | 24 | 89 |
| 5 | dppf | 4 | 100 |

Example 6

Synthesis of an Alcohol:

To a DMF (0.2 mL) solution of CuF.3PPh3.2EtOH (10 mg, 0.01 mmol) as synthesized according to the method described in the foregoing publication and dppf (8 mg, 0.014 mmol) (this catalyst preparation method is designated as "A"; hereinafter the same), benzaldehyde (0.020 mL, 0.20 mmol) and vinyltrimethoxysilane (62 μL, 0.40 mmol) were added at room temperature under an argon atmosphere, the temperature was then raised to 60° C., and the mixture was stirred for 3 hours. Thereafter, the reaction mixture was allowed to stand for cooling to room temperature, to which was then added tetrabutylammonium fluoride (TBAF) (1M/THF, 0.5 mL), and the mixture was stirred for 10 minutes. After adding water, the mixture was extracted with ethyl acetate, and the resulting organic layer was washed with saturated brine and then dried over anhydrous sodium sulfate. After drying, the solvent was distilled off, and the residue was subjected to silica gel column chromatography (ethyl acetate/hexane: 1/9 to 1/4), thereby obtaining desired 1-phenyl-2-propen-1-ol in a yield of 100%.

Examples 7 to 14

The results obtained by carrying out the same operations as in Example 6, except for changing the substrate, are shown in Table 2.

Example 15

Synthesis of an Optically Active Allylic Alcohol:

$CuF_2 \cdot 2H_2O$ (3 mg, 0.020 mmol) and (R)-DTBM-SEGPHOS (47 mg. 0.04 mmol) were added to methanol (0.7 mL) under an argon atmosphere, and the mixture was refluxed for 2 hours. Thereafter, the reaction mixture was allowed to stand for cooling to room temperature, and the volatile matter was removed in vacuo. Toluene (0.5 mL) was added to the resulting residue, and the operation for removal of the volatile matter was again carried out twice in vacuo (this catalyst preparation method is designated as "B"; hereinafter the

TABLE 2

| Example | Substrate | Product | Amount of catalyst (% by mole) | Temperature (° C.) | Time (h) | Yield (%) |
|---|---|---|---|---|---|---|
| 7 | 4-Cl-C6H4-CHO | 4-Cl-C6H4-CH(OH)-CH=CH2 | 5 | 60 | 1 | 81 |
| 8 | 4-Me-C6H4-CHO | 4-Me-C6H4-CH(OH)-CH=CH2 | 5 | 60 | 19 | 81 |
| 9 | Ph-CH=CH-CHO | Ph-CH=CH-CH(OH)-CH=CH2 | 5 | 60 | 6 | 69 |
| 10 | 2-thienyl-CHO | 2-thienyl-CH(OH)-CH=CH2 | 10 | 40 | 26 | 88 |
| 11 | Ph-C(O)-CO2Me | Ph-C(OH)(CH=CH2)-CO2Me | 10 | 40 | 14 | 40 |
| 12 | 4-Cl-C6H4-CHO | 4-Cl-C6H4-CH(OH)-Ph | 5 | 40 | 1 | 71 |
| 13 | 4-Me-C6H4-CHO | 4-Me-C6H4-CH(OH)-Ph | 5 | 40 | 1 | 99 |
| 14 | Ph-CH2-C(Me)2-CHO | Ph-CH2-C(Me)2-CH(OH)-Ph | 5 | 40 | 12 | 50 | same). The resulting CuF-phosphine complex was dissolved in DMF (1 mL), to which were then added benzaldehyde (67 μL, 0.67 mmol) and vinyltrimethoxysilane (206 μL, 1.34 mmol) at room temperature, and the mixture was stirred at 40° C. for 30 minutes. The reaction mixture was allowed to stand for cooling to room temperature, to which was then added tetrabutylammonium fluoride (TBAF) (1M/THF, 0.5 mL), and the mixture was stirred for 10 minutes. After adding water, the mixture was extracted with ethyl acetate, and the resulting organic layer was washed with saturated brine and then dried over anhydrous sodium sulfate. After drying, the solvent was distilled off, and the residue was subjected to silica gel column chromatography (ethyl acetate/hexane: 1/9 to 1/4), thereby obtaining desired 1-phenyl-2-propen-1-ol in a yield of 99%. Its optical purity was measured by HPLC and found to be 94% ee. Furthermore, its absolute configuration was determined in terms of an angle of rotation by comparison with an already reported value. As a result, the product was found to be an (S)-form.

The term "DTBM-SEGPHOS" means ((4,4'-bi-1,3-benzo-dioxole)-5,5'-diyl)bis(bis(3,5-di-t-butyl-4-methoxyphenyl)phosphine).

Examples 16 to 20

The results obtained by carrying out the same operations as in Example 15, except for changing the ligand, are shown in Table 3. The abbreviations have the following meanings. Incidentally, the stereospecific configurations of the resulting products were confirmed in terms of an angle of rotation by comparison with already reported values. As a result, all the products were found to be an (S)-form.

(R)-p-tol-BINAP:
2,2'-Bis[di(p-tolyl)phosphino]-1,1'-binaphthyl (R,R)-CHIRAPHOS:
(2R,3R)-Bis(diphenylphosphino)butane (R,R)-EtDuPHOS:
1,2-Bis((2R,5R)-2,5-diethylphosphorano)benzene (S,S)-iPr-DuPHOS:
1,2-Bis((2S,5S)-2,5-diisopropylphosphorano)benzene

TABLE 3

| Example | Ligand | Catalyst preparation method | Time (h) | Yield (%) | Optical purity (ee %) |
|---------|--------|------------------------------|----------|-----------|------------------------|
| 16 | (R)-p-tol-BINAP | A | 25 | 54 | 49 |
| 17 | (R)-p-tol-BINAP | B | 25 | 47 | 61 |
| 18 | (R,R)-CHIRAPHOS | B | 24 | 24 | 7 |
| 19 | (R,R)-EtDuPHOS | B | 25 | 51 | 38 |
| 20 | (S,S)-iPr-DuPHOS | B | 5 | 87 | 61 |

Examples 21 to 32

Synthesis of an Optically Active Alcohol:

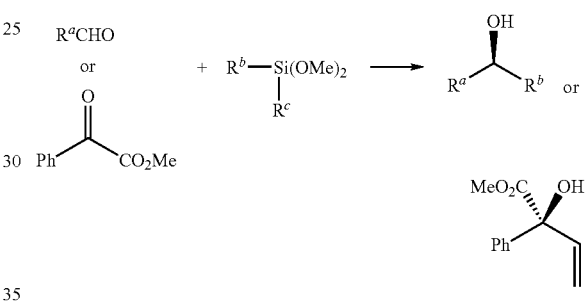

The results obtained by carrying out the same operations as in Example 15, except for changing the substrate and the silane, are shown in Tables 4 and 5.

TABLE 4

| Example | $R^a$ | $R^b$ | $R^c$ | Amount of catalyst (% by mole) | Temperature (° C.) | Time (h) | Yield (%) | Optical purity (ee %) |
|---------|-------|-------|-------|-------------------------------|--------------------|----------|-----------|------------------------|
| 20 | Cl—C6H4— | CH2=CH— | MeO | 3 | 40 | 2 | 99 | 97 |
| 21 | Me—C6H4— | CH2=CH— | MeO | 3 | 40 | 8 | 99 | 99 |
| 22 | MeO—C6H4— | CH2=CH— | MeO | 10 | 40 | 1 | 99 | 92 |
| 23 | 2-thienyl | CH2=CH— | MeO | 10 | 40 | 0.5 | 99 | 91 |
| 24 | Ph-CH=CH— | CH2=CH— | MeO | 10 | 40 | 1 | 73 | 83 |

TABLE 4-continued

| Example | R$^a$ | R$^b$ | R$^c$ | Amount of catalyst (% by mole) | Temperature (°C.) | Time (h) | Yield (%) | Optical purity (ee %) |
| --- | --- | --- | --- | --- | --- | --- | --- | --- |
| 25 | Ph-C(Me)(Me)-CH2- | CH$_2$=CH- | MeO | 10 | 40 | 40 | 99 | 99 |
| 26 | cyclohexyl- | CH$_2$=CH- | Me | 10 | 25 | 16 | 84 | 98 |
| 27 | Ph- | Me(CH$_2$)$_3$CH=CH- | MeO | 10 | 40 | 2.5 | 91 | 90 |
| 28 | Ph-C(Me)(Me)-CH2- | Me(CH$_2$)$_3$CH=CH- | MeO | 10 | 40 | 50 | 90 | 97 |
| 29 | Ph- | CH$_2$=C(CH$_2$)$_2$Me | Me | 10 | 60 | 17 | 48 | 52 |
| 30 | 4-Cl-C$_6$H$_4$- | Ph | Ph | 3 | 40 | 1 | 81 | 92 |
| 31 | 4-Me-C$_6$H$_4$- | Ph | Ph | 5 | 40 | 3 | 83 | 90 |

In Example 29, 10 mole % tetrabutylammonium difluorotriphenylsilicate was added.

TABLE 5

| Example | Substrate | Rb | Rc | Amount of catalyst (% by mole) | Temperature (°C.) | Time (h) | Yield (%) | Optical purity (ee %) |
| --- | --- | --- | --- | --- | --- | --- | --- | --- |
| 32 | Ph-C(=O)-CO$_2$Me | CH$_2$=CH- | MeO | 10 | 25 | 22 | 76 | 84 |

Example 33

Synthesis of (S)-1-phenyl-2-propen-1-ol:

To a DMF (0.3 mL) solution of Cu(O-Bu-t) (20 mg, 0.02 mmol) as synthesized according to the method described in the publication *Inorg. Chim. Acta*, 1981, 20, 2728, (R)-DTBM-SEGPHOS (35 mg, 0.03 mmol) and triethoxysilane fluoride (4.0 μL, 0.02 mmol), benzaldehyde (0.020 mL, 0.20 mmol) and vinyltrimethoxysilane (62 μL, 0.40 mmol) were added at room temperature under an argon atmosphere, the temperature was then raised to 40° C., and the mixture was stirred for 30 minutes. Thereafter, the reaction mixture was allowed to stand for cooling to room temperature, to which was then added tetrabutylammonium fluoride (TBAF) (1M/THF, 0.5 mL), and the mixture was stirred for 10 minutes. After adding water, the mixture was extracted with ethyl acetate, and the resulting organic layer was washed with saturated brine and then dried over anhydrous sodium sulfate. After drying, the solvent was distilled off, and the residue was subjected to silica gel column chromatography (ethyl acetate/hexane: 1/9 to 1/4), thereby obtaining desired 1-phenyl-2-propen-1-ol as an (S)-form in a yield of 65% and an optical purity of 94% ee.

INDUSTRIAL APPLICABILITY

The desired compounds of the invention are useful as intermediates of drugs, agricultural chemicals, and the like.

This application claims priority of Japanese patent application No. 2005-057618 filed Mar. 2, 2005, which is incorporated herein by reference.

What is claimed is:

1. A process for producing an alcohol or a silyl ether thereof represented by the following formula (4):

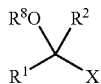
(4)

wherein $R^1$ represents an optionally substituted hydrocarbon group, an optionally substituted heterocyclic group, or an alkoxycarbonyl group; $R^2$ represents a hydrogen atom or $CO_2R$, wherein R represents an alkyl group, an aralkyl group, or an aryl group; X represents an aryl group or an alkenyl group represented by the following formula (3):

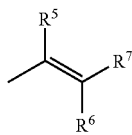
(3)

wherein $R^5$, $R^6$ and $R^7$ each independently represents a hydrogen atom or an alkyl group; and $R^5$ and $R^6$ may be taken together to form a methylene chain; and $R^8$ represents a hydrogen atom or a silyl residue of a silane represented by the following formula (2):

$$(R^3)_2R^4Si-X \quad (2)$$

wherein $R^3$ represents an alkyl group or an alkoxy group; $R^4$ represents an alkyl group, an alkoxy group, or an aryl group; and X is the same as defined above, which comprises reacting a compound represented by the following formula (1):

$$R^1(C=O)R^2 \quad (1)$$

wherein $R^1$ and $R^2$ are the same as defined above, with the silane represented by the foregoing general formula (2) in the presence of (i) a catalyst component containing copper fluoride or a catalyst component containing a copper compound and a fluoride and (ii) a bidentate phosphine compound, or in the presence of a complex obtained from (i) and (ii).

2. The process according to claim 1, wherein the bidentate phosphine compound is optically active, and the compound of the formula (4) is an optically active substance.

* * * * *